United States Patent [19]

Grayson et al.

[11] Patent Number: 5,276,191
[45] Date of Patent: Jan. 4, 1994

[54] PROCESS FOR THE PREPARATION OF KETONES

[75] Inventors: James I. Grayson; Graham Heyes, both of Durham City, England

[73] Assignee: Fine Organics Limited, London, England

[21] Appl. No.: 783,685

[22] Filed: Oct. 29, 1991

Related U.S. Application Data

[63] Continuation of Ser. No. 623,111, Dec. 8, 1989, abandoned.

[30] Foreign Application Priority Data

Dec. 8, 1989 [GB] United Kingdom ........... 8927864.2

[51] Int. Cl.$^5$ ............................................ C07C 211/00
[52] U.S. Cl. ...................................................... 564/343
[58] Field of Search ................. 564/343; 568/309, 335, 568/336, 337

[56] References Cited

U.S. PATENT DOCUMENTS

2,585,988 2/1952 Asscher ................................ 564/343
3,833,677 9/1974 Grard ................................... 568/337
4,952,729 8/1990 Babad et al. ........................ 568/337

FOREIGN PATENT DOCUMENTS

0218354 11/1985 Japan .

OTHER PUBLICATIONS

Asscher II "A new synthesis of ω-amino-p-hydroxyacetophenones etc.", *Recueil travaux chimiques Pays-Bas* 68 (1949)960-8.
Asscher et al. III "Synthesis of β-phenyl-ethylamine derivatives, II." Receuil travaux chimiques *Pays-Bas* 71 (1952) 933-43.

*Primary Examiner*—Allen J. Robinson
*Assistant Examiner*—P. O'Sullivan
*Attorney, Agent, or Firm*—Larson and Taylor

[57] ABSTRACT

According to the invention, there is provided a process for the preparation of an aminoalkyl p-hydroxyphenyl ketone comprising reacting phenol with a nitrile, in the presence of a Lewis acid catalyst, to cause condensation thereof, the process being characterised in that the reaction is carried out in a medium comprising a nitroalkane solvent for the reactants.

11 Claims, No Drawings

PROCESS FOR THE PREPARATION OF KETONES

This application is a continuation of application Ser. No. 07/623,111, filed Dec. 6, 1990, now abandoned.

The present invention relates to the preparation of aminoalkyl p-hydroxyphenyl ketones.

Certain aminoalkyl p-hydroxyphenyl ketones are important intermediates in the production of compounds having pharmaceutical activity. In particular aminoalkyl p-hydroxyphenyl ketones such as the compounds denoted by the general formula:

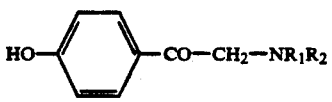

I wherein $R_1$ and $R_2$ denote hydrogen atoms, alkyl radicals containing 1 to 5 carbon atoms or aryl radicals (the 2'amino 4-hdyroxyacetophenones) may be converted by known methods, e.g. by catalytic hydrogenation, to compounds denoted by the formula:

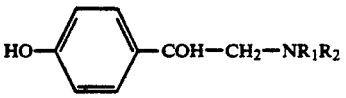

II where $R_1$ and $R_2$ denote hydrogen (octopamine) or where $R_1$ denotes hydrogen and $R_2$ denotes the methyl radical (synephrine) which compounds are known as pharmaceuticals.

The present invention relates particularly to the above-identified family of ketones. However, operative closely related derivatives, for example derivatives selected from those in which a methylene group hydrogen is substituted by an alkyl radical containing 1 to 5 carbon atoms or a cycloalkyl or an aryl radical are considered to be within the scope of the present invention.

The known Houben-Hoesch reaction is a variation of the Friedel-Crafts reaction and involves the condensation of a phenolic substrate with a nitrile in the presence of a Lewis acid catalyst to give a hydroxy-aryl ketone. It has been extensively reviewed, e.g. by W. Ruske in Olah, Friedel-Crafts Reactions Vol 3 (1964), and P. E. Spoerri and A. S. Dubois, in Organic Reactions Vol 5 (1949). It is known that the reaction is very efficient with poly-hydroxybenzenes such as resorcinol or phloroglucinol, needing only mild conditions such as $ZnCl_2$ in ether, but these conditions fail with phenol, only the phenyl acetimidates being formed. Phenol requires aluminium chloride as catalyst to undergo the Houben-Hoesch reaction and then only with relatively active nitriles such as tirchloroacetonitrile. When a less reactive nitrile, such as aminoacetonitrile is required to react with phenol, then even more forcing conditions are needed. M. Asscher, in U.S. Pat. No. 2,585,988 (1952) and in Receuil travaux chimiques Pays-Bas, 68, 960 (1949) and 71, 933 (1952), describes the condensation of phenol, anisole or benzylphenyl ether with aminoacetonitriles, bearing various substituents on the amino group. The reaction is reported not to work with amino substituted propionitriles or higher nitriles. Asscher found that the usual conditions of $ZnCl_2$/ether or $AlCl_3$ in ether or chlorobenzene gave no or little product in this reaction; however the reaction proceeded well in nitro-aromatic solvents, such as nitrobenzene, o-nitrotoluene or o-nitroanisole. The reaction described by Asscher may be summarised by the reaction scheme:

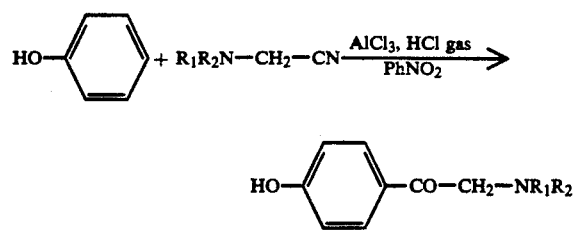

in which Ph denotes the phenyl radical.

In Asscher's patent, U.S. Pat. No. 2,585,988, he claims this reaction with nitrobenzene and chlorobenzene as solvents (claim 1). However in example 3 of the same patent, the reaction of phenol and N-methylaminoacetonitrile in chlorobenzene solvent is described, but giving only a 19% yield of the compound of general formula I (R1=Me, R2=R3=H). For the reaction of aminoacetonitrile hydrochloride and phenol with aluminium chloride in nitrobenzene, an isolated yield of 51% is quoted for the free base of the aminoketone of the general formula I (R1=R2=R3=H). Asscher also uses hydrogen chloride gas as a promoter for the reaction and determines the optimum amount of $AlCl_3$ used as 2.25 moles per mole of starting nitrile.

In attempting to repeat the work of Asscher, we have found a number of problems. In the first place, the use of nitrobenzene is not recommended because, unlike Asscher, we have found that the reaction mixture is not homogeneous and foaming can be a problem when the hydrogen chloride gas is emitted. This is because the aminonitrile and aluminum chloride do not form a soluble complex in nitrobenzene and the nitrobenzene thus has to be present in a large excess to control this foaming. Nitrobenzene is also unsuitable because of its toxicity, having a TWA of 1 ppm. Furthermore the use of mixtures of nitrobenzene, aluminum chloride and phenol has been shown to be hazardous (Chem. Eng. News 1953, 31, 4915). We were able to achieve a yield of only 45–50% when repeating the reaction of aminoacetonitrile and phenol under the conditions described by Asscher, the aminoketone formed having a purity of <95% by non-aqueous titration. The use of chlorobenzene alone was also found to be unsuitable as no compound of general formula I was found. The reaction mixture is also not homogeneous in chlorobenzene.

It is an object of the present invention to provide a new or improved process for the manufacture of aminoalkyl p-hydroxyphenyl ketones.

According to the present invention, there is provided a process for the preparation of an aminoalkyl p-hydroxyphenyl ketone comprising reacting phenol with a nitrile, in the presence of a Lewis acid catalyst, to cause condensation thereof, the process being characterised in that the reaction is carried out in a medium comprising a nitroalkane solvent for the reactants.

A preferred but non-limiting feature of the invention is the production of 2'amino-4-hydroxyacetophenones, the nitrile being that denoted by the general formula:

$R_1R_2N-CH_2-CN$ wherein $R_1$ and $R_2$ denote hydrogen atoms, alkyl radicals containing 1 to 5 carbon atoms, cycloalkyl radicles or aryl radicals, but particularly preferably hydrogen atoms or methyl radicals.

In carrying out the present invention, the nitriles and the aminoalkyl p-phenylketones produced may be in the strong inorganic acid form and this is understood to be within the invention as expressed herein.

The present invention is based on the surprising discovery that nitroalkanes are unexpectedly much better solvents for this reaction, being less toxic, giving a better yield and also ensuring a homogeneous reaction medium. The nitroalkanes may also be diluted with a halogenated hydrocarbon solvent, which acts as an inert diluent, thus reducing the amount of nitroalkane used, and making the reaction less hazardous. This is despite the fact that the chlorinated hydrocarbons may in themselves be unsuitable as sole solvents for the reaction because they do not permit the formation of a soluble complex of the starting aminonitrile with aluminium chloride. The quantity of nitroalkane required is as little as one mole equivalent based on the aluminium chloride, which is considerably less than the 2.2 mole equivalents of nitrobenzene used in the said U.S. patent.

The nitroalkane used is preferably a lower aliphatic nitroalkane, desirably one which is commercially available, such as nitromethane, nitroethane, 2-nitropropane or 1-nitropropane. The amount of nitroalkane required is a minimum of 1 mole per mole aluminium chloride. Preferably we use 1.0-2.5 moles nitroalkane per mole aluminium chloride, most preferably 1.2-1.6 moles.

As stated above, the nitroalkane is preferably mixed with a chlorinated hydrocarbon such as dichloromethane, 1,2-dichloroethane, chlorobenzene or 1,2-dichlorobenzene. The quantity of chlorinated hydrocarbon is preferably 1-3 parts per part nitroalkane, parts being by weight.

The amount of phenol is preferably at least one mole per mole aminoacetonitrile hydrochloride, and preferably 1.1-1.5 moles.

The amount of aluminium chloride used is preferably 2.0-2.5 moles per mole aminoacetonitrile hydrochloride. The amount of hydrogen chloride gas used is preferably 1-2 parts per part aminoacetonitrile hydrochloride.

The preferred reaction temperature is 10°-30° C., and the preferred reaction time after addition of the hydrogen chloride gas is 3 to 18 hrs.

The work-up procedure given in U.S. Pat. No. 2,585,988 and claimed in claim 2 of that patent is not necessary with our process. It is thus not necessary to react the hydrochloride of the compound produced by the reaction with an aqueous solution of an organic hydroxy-acid or its salt, e.g. lactate, tartrate, or citrate in order to maintain the aluminum ions in solution, and then to precipitate the amino-ketone as its free base. Instead the reaction mixture, after a suitable equilibration period which may for example be from 1 hour to 48 hours or more, may be mixed with water to precipitate the product which may often be sufficiently pure for further processing, e.g. by hydrogenation but, if required, it can be further purified by standard methods, e.g. by recrystallisation.

The process of the invention is further described by the following examples.

Example 1.

2'-Amino-4-hydroxyacetophenone hydrochloride. A suspension of aminoacetonitrile hydrochloride (50 g) and phenol (62.6 g) in nitromethane (250 g) was stirred at 15°-20° C., and aluminium chloride (175 g) was added with stirring and cooling. Hydrogen chloride gas (78 g) was added over a period of 3 hrs while the temperature was maintained at 15° C. The subsequent clear solution was left to stand for 18 hrs at 20° C., and was then poured slowly into 400 ml of water, cooled to prevent the temperature rising above 30° C. The precipitate of 2'-amino-4-hydroxyacetophenone hydrochloride was filtered off, washed with isopropanol, and dried. The yield of 2'-amino-4-hydroxyacetophenone hydrochloride was 72.7 g (71.8%), having a purity of 97% by non-aqueous titration.

EXAMPLES 2-9.

These were performed essentially as example 1, except the solvents used and the yields obtained were as shown in the Table, all weights being in grams.

TABLE

| Ex. | Solvent | wt | Diluent | wt | Yield wt | Yield % | Purity % |
|---|---|---|---|---|---|---|---|
| 2 | nitroethane | 250 | none | | 72.0 | 70.7 | 99 |
| 3 | 2-nitropropane | 250 | none | | 64.9 | 63.1 | 95 |
| 4 | nitromethane | 160 | 1,2-dichlorobenzene | 250 | | 78.5 | |
| 5 | nitromethane | 162 | chlorobenzene | 252 | | 71.2 | |
| 6 | 2-nitropropane | 160 | 1,2-dichloroethane | 250 | | 51.5 | |
| 7 | nitromethane | 120 | 1,2-dichloroethane | 200 | | 77.1 | |
| 8 | nitroethane | 122 | 1,2-dichloroethane | 300 | | 63.5 | |
| 9 | nitroethane | 175 | dichloromethane | 300 | | 58.6 | |

We claim:
1. A process for the preparation of an aminoalkyl p-hydroxyphenyl ketone comprising reacting phenol with a nitrile, in the presence of a Lewis acid catalyst, to cause condensation thereof, the process being characterised in that the reaction is carried out in a medium comprising a nitroalkane solvent for the reactants.

2. A process as claimed in claim for the production of 2'amino-4-hydroxyacetophenones, wherein the nitrile is that denoted by the general formula

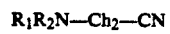

$R_1R_2N-CH_2-CN$ wherein $R_1$ and $R_2$ denote hydrogen atoms, alkyl radicals containing 1 to 5 carbon atoms, aryl radicals or cycloalkyl radicals.

3. A process as claimed in claim 2, wherein the nitrile is that denoted by the general formula and in which $R_1$ and $R_2$ denote hydrogen atoms or methyl radicals.

4. A process according to claim 1, wherein the nitroalkane used is a lower aliphatic nitroalkane.

5. A process according to claim 4, wherein the nitroalkane is nitromethane, nitroethane, or a hitropropane.

6. A process according to claim 1 wherein the Lewis acid catalyst is aluminum chloride and the amount of nitroalkane is 1.0-2.5 moles nitroalkane per mole aluminium chloride.

7. A process according to claim 6, wherein the amount of nitroalkane is 1.2–1.6 moles nitroalkane per mole aluminum chloride.

8. A process according to claim 1, wherein the nitroalkane is diluted with a chlorinated hydrocarbon.

9. A process according to claim 8, wherein the chlorinated hydrocarbon is dichloromethane, 1,2-dichloroethane, chlorobenzene or 1,2-dichlorobenzene.

10. A process according to claim 8 wherein the quantity of chlorinated hydrocarbon is 1–3 parts per part nitroalkane, the parts being by weight.

11. A process according to claim 1 wherein the nitrile is aminoacetonitrile hydrochloride and the amount of phenol is 1.1–1.5 moles per mole aminoacetonitrile hydrochloride.

* * * * *